United States Patent [19]

Willis

[11] Patent Number: 5,152,789
[45] Date of Patent: Oct. 6, 1992

[54] FIXATION MEMBER FOR AN INTRAOCULAR LENS

[75] Inventor: Timothy R. Willis, Lake Forest, Calif.

[73] Assignee: Allergan, Inc., Irvine, Calif.

[21] Appl. No.: 699,496

[22] Filed: May 14, 1991

[51] Int. Cl.$^5$ .................................. A61F 2/16
[52] U.S. Cl. ................................................ 623/6
[58] Field of Search ...................................... 623/6

[56] References Cited

U.S. PATENT DOCUMENTS

| | | | |
|---|---|---|---|
| 2,714,721 | 8/1955 | Stone, Jr. | 623/5 |
| 4,655,775 | 4/1987 | Clasby, III | 623/6 |
| 4,693,715 | 9/1987 | Abel, Jr. | 623/5 |
| 4,804,361 | 2/1989 | Anis | 623/6 |
| 4,888,013 | 12/1989 | Ting et al. | 623/6 |

FOREIGN PATENT DOCUMENTS 2124500A  2/1984  United Kingdom ............ 623/6

*Primary Examiner*—Ronald Frinks
*Attorney, Agent, or Firm*—Gordon L. Peterson

[57] ABSTRACT

An intraocular lens comprising a deformable optic and a fixation member for use in supporting the optic in the eye. The fixation member includes an annulus surrounding the optic and a plurality of resilient struts interconnecting the optic with the annulus. The struts tend to be compressively loaded by the posterior capsule of the eye after implantation. To prevent buckling of the resilient struts in an axial direction due to the imposed compressive loads, the struts are curved in a circumferential direction when in an unloaded state, thereby being predisposed to further bow in the same circumferential direction upon imposition of the compressive load. This predisposition to bow circumferentially avoids severe problems incurred if the struts are permitted to buckle axially, such as tilting of the optic and impaired vision for the patient.

7 Claims, 1 Drawing Sheet

FIXATION MEMBER FOR AN INTRAOCULAR LENS

FIELD OF THE INVENTION

This invention relates to an intraocular lens and, more particularly, to an intraocular lens having a deformable optic which is supported by a resilient, deformable fixation member configured to minimize an undesirable tipping of the optic.

BACKGROUND OF THE INVENTION

Whenever cataracts or other conditions require, the natural lens of the human eye can be removed and replaced with an intraocular lens. An intraocular lens comprises an optic or lens and one or more fixation members for fixing the lens in the proper position within the eye so that the optic can direct light toward the retina.

In one common form of intraocular lens, the optic is constructed of a hard, non-deformable material, such as polymethylmethacrylate (PMMA). In a second type of intraocular lens, the optic is constructed of a deformable material, such as silicone or hydrogel. A deformable optic can be rolled or folded for insertion through an incision into the eye. An important advantage of an intraocular lens having a deformable optic is that, when it is rolled or folded, it can be inserted through a relatively small incision into the eye. This reduces the trauma to the patient and provides other advantages.

One problem with an intraocular lens having a deformable optic is in supporting it in an acceptable manner within the eye. One prior art approach is to employ fixation members which are integral with the optic. However, because of the soft, deformable nature of the optic material, it is necessary to make the integral fixation members relatively thick in order that they will have sufficient thickness to adequately retain and position the optic within the eye. Without this necessary thickness, the fixation members may buckle under the generally radial compressive load imposed by the posterior capsule as the posterior capsule shrinks following removal of the natural lens. This causes the optic to tip unacceptably, causing the image being transmitted through the optic to be deflected away from the retina, resulting in blurred and unreliable vision. The problem is that thickening of the integral fixation members gives the rolled or folded intraocular lens a larger cross-sectional area than would exist without such thickening, and this, in turn, requires a larger incision.

Another approach is to utilize separate fixation members and attach them to the optic. These separate fixation members, which are commonly constructed of PMMA or polypropylene, are typically fine hair-like strands. It is somewhat difficult to attach these fine hair-like strands to a deformable optic in a way that will assure that the strands will not pull out from the deformable optic.

What is needed is a support system for a deformable intraocular lens wherein a fixation member is easily attached to the optic and has the characteristics necessary to ensure that the optic does not tend to tilt undesirably in the manner described above.

SUMMARY OF THE INVENTION

This invention solves the problem outlined above for an intraocular lens having a resiliently deformable optic for implantation into an eye. An annular fixation member or support of resilient deformable material for supporting the optic in the eye is coupled to, and circumscribes, the optic and has within it a plurality of elongated openings. These elongated openings, while not unacceptably weakening the fixation member, render the fixation member less bulky and more capable of being rolled or folded more tightly, in order to allow the intraocular lens to be inserted through a small incision when being placed into the eye. Preferably, the annular fixation member is integrally molded to the optic, in order to eliminate the problem of having to attach the two elements.

A particularly novel feature of the invention is that the annular fixation member is configured to deform in a generally circumferential direction rather than in an axial direction when it is placed under a compressive load of the type applied by the capsular bag of the eye in which the optic is implanted. These compressive forces are directed from the radial outward end of the fixation member toward the optic. By configuring the fixation member to resiliently flex or deform in a generally circumferential direction, tipping of the optic in response to these forces is virtually eliminated, and normal vision may be maintained.

Specifically, the annular fixation member comprises an annulus and at least one resiliently deformable strut which has a proximal end portion attached to the optic and a distal end portion attached to an annulus. The strut is predisposed to bow circumferentially rather than axially when placed under the compressive load. This predisposition is accomplished by curving or bowing the strut a predetermined amount in a circumferential direction when it is in an unloaded condition, thereby giving the strut the predisposition to bow circumferentially when under load. In a preferred embodiment, a plurality of struts are employed, with the struts being arranged in spoke-like fashion around the periphery of the optic. Each of the struts is preferably bowed a predetermined amount when in an unloaded condition.

The fixation member struts can be in several different configurations. For example, in one preferred configuration, the struts are paired, with the proximal ends and the distal ends of the two struts in each pair being closely spaced at their attachment locations on the optic and on the annulus, respectively. The two struts in each pairing are bowed in opposite circumferential directions with respect to one another. In this configuration, the elongated openings are formed between the two struts in each pairing. In another configuration, the struts are all bowed in the same circumferential direction. The elongated openings lie between adjacent struts.

In another aspect of the invention, the intraocular lens comprises a deformable optic for implantation into an eye and a resiliently deformable support for supporting the optic in the eye. The support includes an annulus which circumscribes the optic and a plurality of struts which integrally join the optic and the annulus. Each of the struts bows circumferentially in response to a compressive load applied generally along the struts from the annulus toward the optic.

The invention, together with additional features and advantages thereof may best be understood by reference to the following description taken in connection with the accompanying illustrative drawing.

DESCRIPTION OF THE PREFERRED EMBODIMENT

Figure 1:
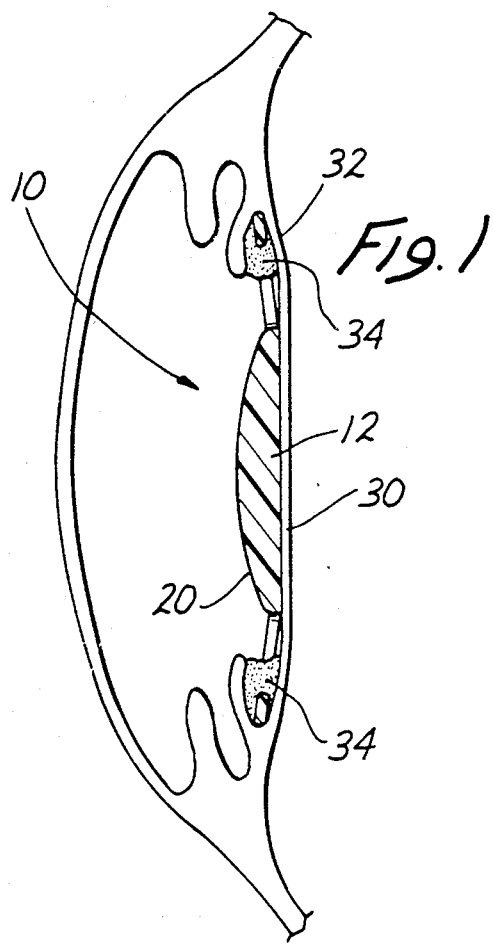
FIG. 1 is a sectional view illustrating an intraocular lens implanted in the posterior capsule of a human eye.
Figure 1A:
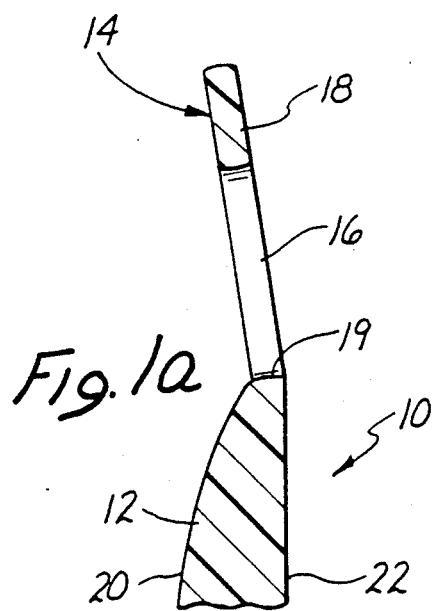
FIG. 1a is an enlarged, fragmentary sectional view illustrating a portion of the intraocular lens of FIG. 1 prior to implantation.
Figure 2:
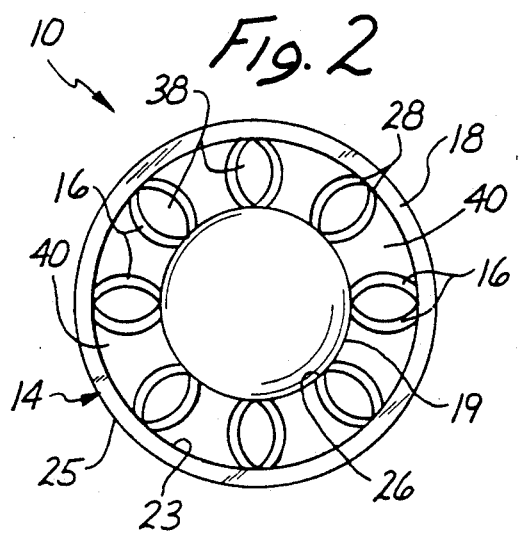
FIG. 2 is a plan view of one embodiment of an intraocular lens constructed in acccordance with this invention.

FIGS. 1, 1a and 2 show an intraocular lens 10 which includes a deformable optic 12 and a resilient, deformable fixation member or support 14 integral with the optic. The fixation member 14 comprises a plurality of struts 16 and an annular member or annulus 18.

The optic 12 may be of any suitable configuration and, in this embodiment, is circular as viewed in plan and has a circular periphery 19. The optic 12 has an anterior surface 20 and a posterior surface 22. In this embodiment, the anterior surface 20 is convex, and the posterior surface 22 is planar; however, these configurations are purely illustrative.

The annulus 18 is generally circular and circumscribes the optic 12. The annulus 18 has a circular inner periphery 23 and a circular outer periphery 25 which defines the outer periphery of the intraocular lens 10. The annulus 18 is resiliently deformable and is in the form of a thin, circular web having a relatively short radial dimension.

Each of the struts 16 have a proximal end 26 and a distal end 28. The struts 16 interconnect the optic 12 with the annulus 18. Each of the struts 16 is elongated and resilient and is capable of being folded or rolled very compactly when the intraocular lens 10 is to be inserted into the eye, thereby permitting insertion through a very small incision. The proximal end 26 of each strut is attached to the optic 12, while the distal end 28 of each strut is attached to the annulus 18. In the preferred embodiment, the optic 12, the struts 16, and the annulus 18 are all integrally molded of either silicone or hydrogel, both very pliable and resilient materials.

The fixation member 14 extends generally radially from the periphery 19 of the optic 12. Although the fixation member 14 may lie in a perfectly radial plane, as shown in FIGS. 1 and 1a, the fixation member 14 is inclined anteriorly a few degrees. Accordingly, after implantation of the intraocular lens in the eye as shown by way of example in FIG. 1, the optic 12 is urged posteriorly against a posterior wall 30 of a posterior capsule 32 of the eye.

After surgical implantation of the intraocular lens 10 into the eye, the posterior capsule 32 will tend to grow together between the struts 16 as represented by the shaded portion 34 in FIG. 1. In addition, the posterior capsule 32 shrinks radially, and this shrinkage exerts a generally radial compressive force on the annulus 18, which is transmitted to the optic 12 along the struts 16. Without compensating for these forces, the resilient struts 16 may deform in an axial direction, i.e., in a direction generally parallel to the optical axis 36 of the intraocular lens 10. This is extremely undesirable since it may well cause the optic to tilt a sufficient distance to deleteriously affect vision, with the optic 12 no longer properly focusing light on the retina (not shown).

FIG. 2 shows a preferred embodiment of the invention depicting one means for compensating for the compressive forces exerted upon the fixation member 14. In this embodiment, struts 16 are arranged in a spoke-like fashion around the optic 12 and are paired. The proximal ends 26 of the two struts in each pair are very closely spaced at their attachment locations to the optic 12 as shown in FIG. 2. Similarly, the distal ends 28 of the two struts are very closely spaced at their attachment points on the annulus 18. Significantly, the two struts 16 in each pairing are bowed symmetrically in opposite circumferential directions with respect to one another, i.e., the struts are concave toward each other. The struts 16 are bowed in a circumferential direction even when in an unloaded condition prior to being placed under compressive stress by the posterior capsule, and are in fact manufactured to be "pre-bowed" a predetermined amount. Between the two struts in each pairing are radially elongated openings 38 which extend radially between the optic 12 and the annulus 18. The adjacent strut pairings are spaced circumferentially to provide openings 40.

It has been discovered that curving or bowing the struts 16 in a circumferential direction while unloaded and prior to insertion of the intraocular lens 10 into the eye predisposes them to bow even more in that same circumferential direction when compressively loaded, rather than bowing or buckling in an axial direction. This is advantageous because bowing the struts 16 circumferentially rather than axially does not cause the optic 12 to be tilted or tipped. Further advantages are gained by pairing the struts 16 and causing the two struts in each pair to bow in opposite circumferential directions since this approach tends to "cancel out" any circumferential forces imposed by the struts on the optic.

Figure 3:
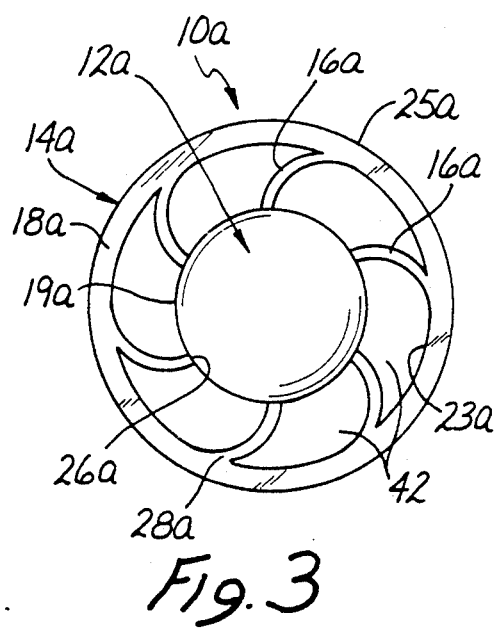
FIG. 3 is a plan view of a second embodiment of an intraocular lens constructed in accordance with this invention.

FIG. 3 shows a second preferred embodiment which is identical in all respects with that of FIG. 2, except as described or shown herein. Each of the elements in FIG. 3 corresponding to equivalent elements in FIG. 2 are designated by the same reference numeral, followed by the letter "a." Thus, in FIG. 3, intraocular lens 10a is comprised of an optic 12a and a fixation member 14a for supporting the optic 12a in the posterior capsule of the eye. The fixation member 14a is further comprised of an annulus 18a and a plurality of struts 16a, which interconnect the optic 12a with the annulus 18a. In this embodiment, the struts 16a are arranged in spoke-like fashion around the optic 12a as in the embodiment of FIG. 2 and are spaced substantially uniformly. Each strut 16a is curved or bowed in the same circumferential direction when in an unloaded condition and is, therefore, predisposed to bow even farther in that same direction when compressively loaded in a generally radial direction. The effect is that the struts 16a resemble a set of turbine vanes surrounding the optic 12a. Circumferentially elongated openings 42 lie between adjacent struts 16a and extend radially and somewhat circumferentially between the optic 12a and the annulus 18a. This embodiment provides the same major advantages as those provided by the FIG. 2 embodiment, including the substantial elimination of an undesirable tipping of the optic 12a due to axial deformation of the struts 16a.

Although exemplary embodiments of the invention have been shown and described, many changes, modifications and substitutions may be made by one having ordinary skill in the art without necessarily departing from the spirit and scope of this invention.

I claim:

1. An intraocular lens for implantation into an eye comprising:

a deformable optic;

an annular fixation member of resilient deformable material for supporting said optic in the eye, said fixation member being coupled to and circumscribing said optic;

said fixation member having a plurality of openings therein, said openings being elongated; and the fixation member including an annulus and a plurality of resiliently deformable struts arranged in spoke-like fashion around the periphery of said optic, said struts being attached to the optic and the annulus, said struts being paired with the proximal ends and the distal ends of the two struts in each pair thereof being closely spaced at their attachment locations to the optic and to the annulus, respectively, and said two struts in each of said pairs being curved in opposite circumferential directions with respect to one another.

2. The intraocular lens as defined in claim 1 wherein said annular fixation member and said optic are integrally molded.

3. The intraocular lens as defined in claim 1 wherein said optic, said strut, and said annulus are all integrally molded of a material selected from the group consisting of silicone and hydrogel.

4. The intraocular lens as defined in claim 1 wherein said elongated openings are formed between the two struts in each pairing thereof.

5. An intraocular lens for implantation into an eye comprising:

a deformable optic;

a resiliently deformable support for supporting said optic in the eye and including an annulus circumscribing said optic and a plurality of struts integrally joining the optic and the annulus;

each of said struts being adapted to bow circumferentially in response to a compressive load applied generally along said struts from the annulus toward the optic; and each of said struts having a proximal end attached to said optic and a distal end attached to said annulus, said struts being paired with the proximal ends and the distal ends of the two struts in each pair thereof being closely spaced at their attachment locations on the optic and on the annulus, respectively, and said two struts being curved in opposite circumferential directions with respect to one another.

6. The intraocular lens as defined in claim 5 wherein said optic, said struts, and said annulus are all integrally molded together.

7. The intraocular lens as defined in claim 6 wherein said optic, said struts, and said annulus are all integrally molded of a material selected from the group consisting of silicone and hydrogel.

* * * * *